(12) United States Patent
Durkin et al.

(10) Patent No.: US 6,230,704 B1
(45) Date of Patent: May 15, 2001

(54) INHALATION DEVICE

(75) Inventors: Jason Durkin, Raleigh; John Parsons, Cary, both of NC (US)

(73) Assignee: Bespak PLC, King's Lynn (GB)

( * ) Notice: Subject to any disclaimer, the term of this patent is extended or adjusted under 35 U.S.C. 154(b) by 0 days.

(21) Appl. No.: 09/380,395

(22) PCT Filed: Mar. 19, 1998

(86) PCT No.: PCT/GB98/00827

§ 371 Date: Oct. 13, 1999

§ 102(e) Date: Oct. 13, 1999

(87) PCT Pub. No.: WO98/42395

PCT Pub. Date: Oct. 1, 1998

(30) Foreign Application Priority Data

Mar. 25, 1997 (GB) .................................................. 9706121

(51) Int. Cl.$^7$ .................................................. A61M 15/00
(52) U.S. Cl. .................................. 128/200.22; 128/200.14; 128/200.18; 128/200.23; 128/203.12; 128/203.23
(58) Field of Search ........................ 128/200.14, 200.18, 128/200.23, 203.12, 203.23, 200.22

(56) References Cited

U.S. PATENT DOCUMENTS

| 3,191,867 | 6/1965 | Helms . |
|---|---|---|
| 3,994,421 | 11/1976 | Hansen . |
| 5,505,194 | 4/1996 | Adjei et al. . |

FOREIGN PATENT DOCUMENTS

| 0 009 667 | 4/1980 | (EP) . |
|---|---|---|
| WO 92 20391 | 11/1992 | (WO) . |

Primary Examiner—Glenn K. Dawson
Assistant Examiner—Mital Patel
(74) Attorney, Agent, or Firm—Smith, Gambrell & Russell

(57) ABSTRACT

An inhalation device (10) for use with an aerosol container comprises a housing (11) for receiving an aerosol container (12) and a spacer member (13) having a mouthpiece (14) defining an outlet (15) through which a user can inhale. The housing and the spacer member are attached together so as to be movable with respect to each other between an inoperative position in which the housing is received within the spacer member and an operative position in which the housing is withdrawn from the spacer member and oriented at a substantial angle thereto. The device further comprises a dispensing member (16) for receiving material to be dispensed from the container and delivering it into the spacer member. The dispensing member (16) is located in the housing and supported spaced from the walls thereof by a plurality of spaced ribs (19). The housing includes a forwardly extending projection (25) shaped so as to be received by the mouthpiece member in the inoperative condition so that the projection acts as a closure member to close the outlet (15).

7 Claims, 4 Drawing Sheets

Figure 8:
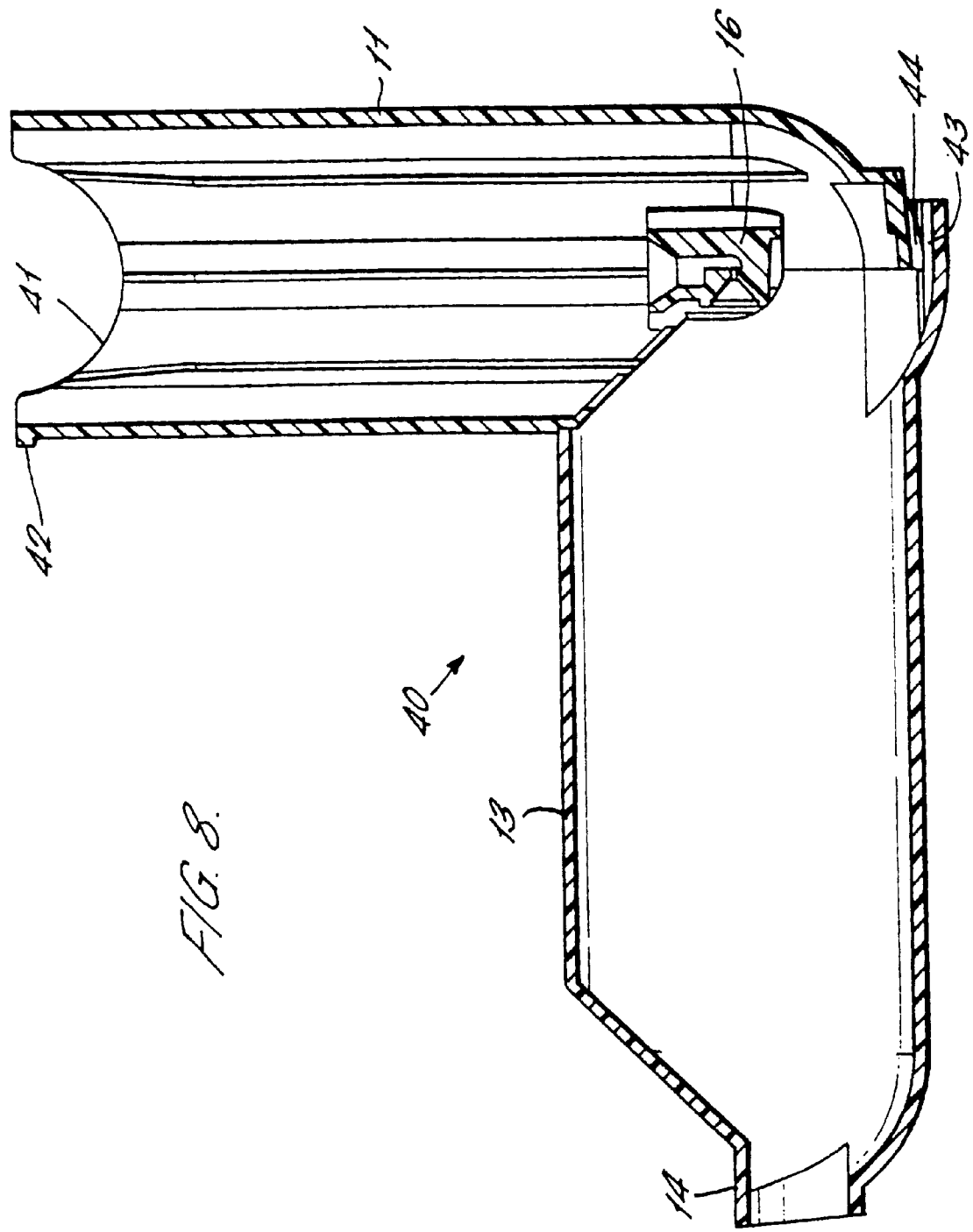

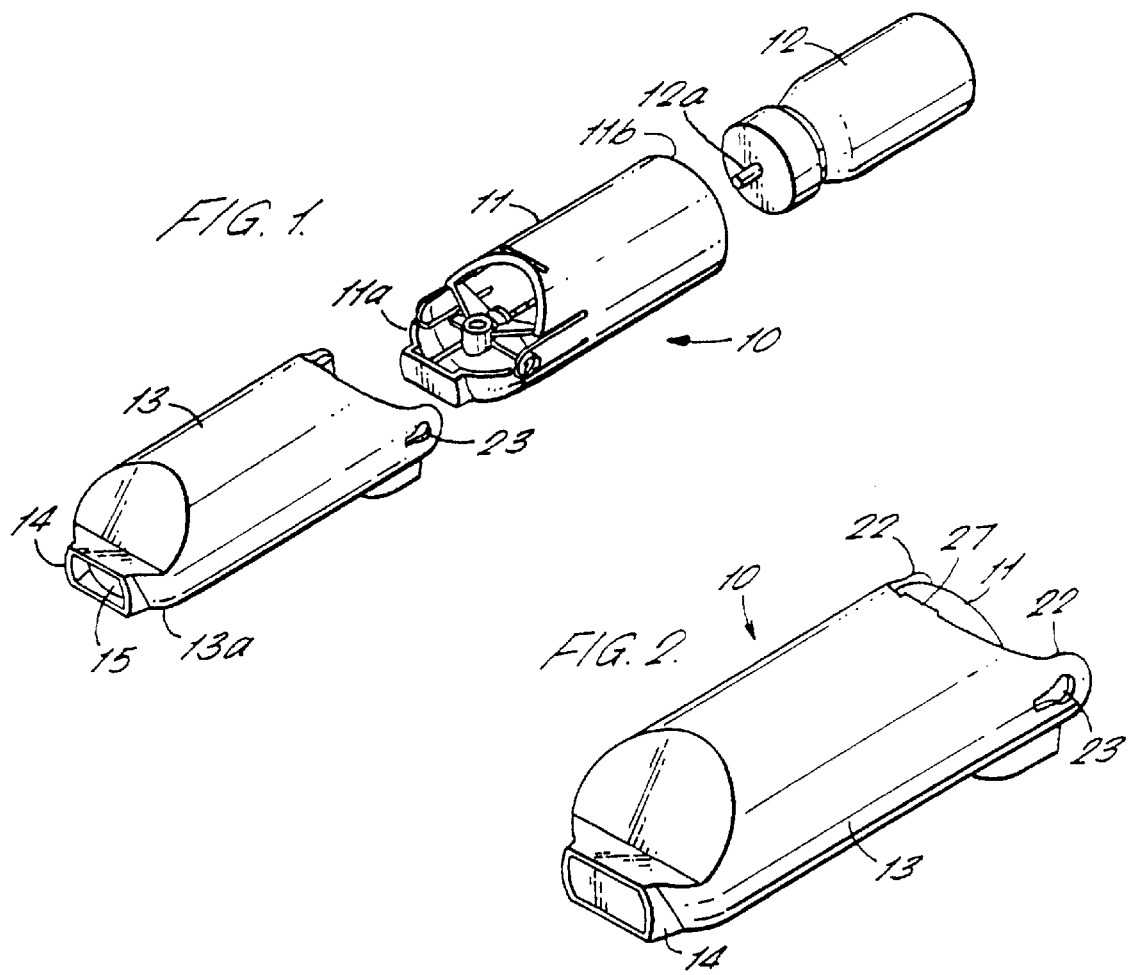
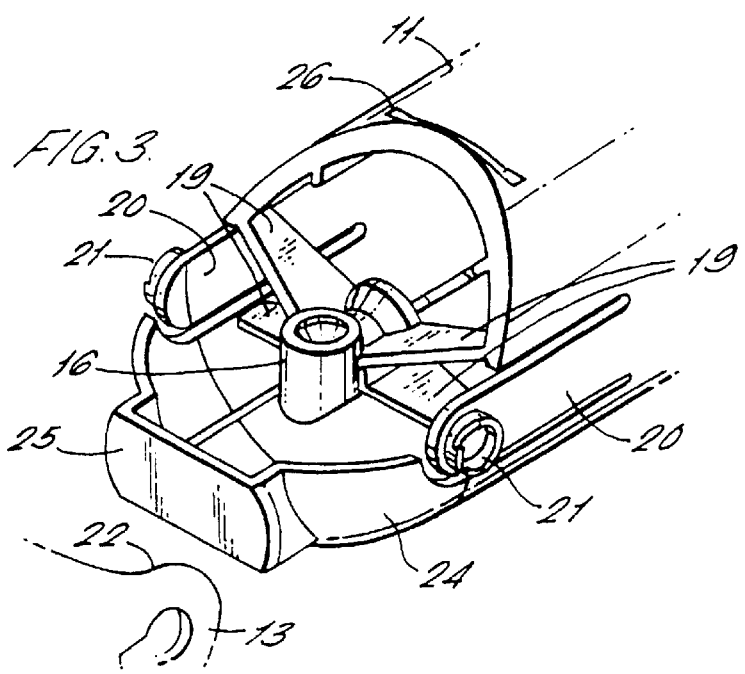

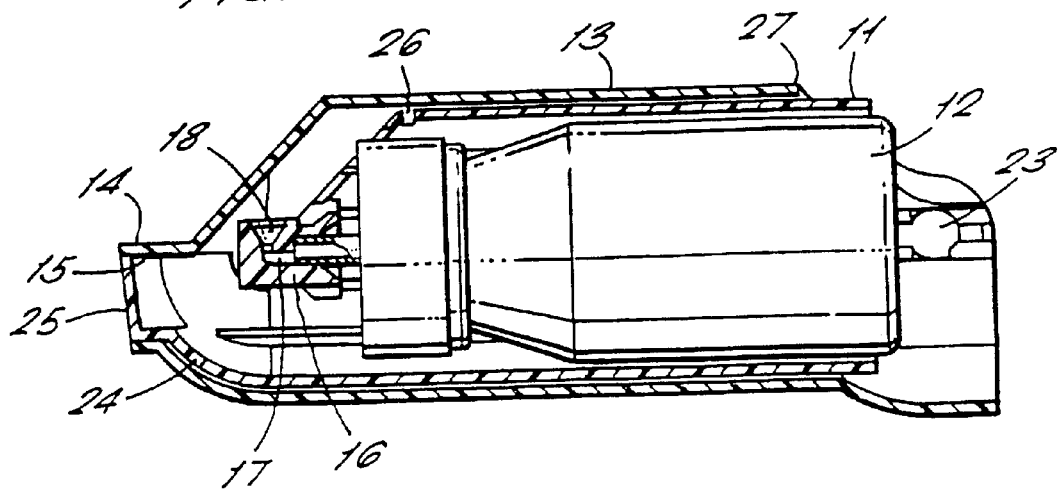
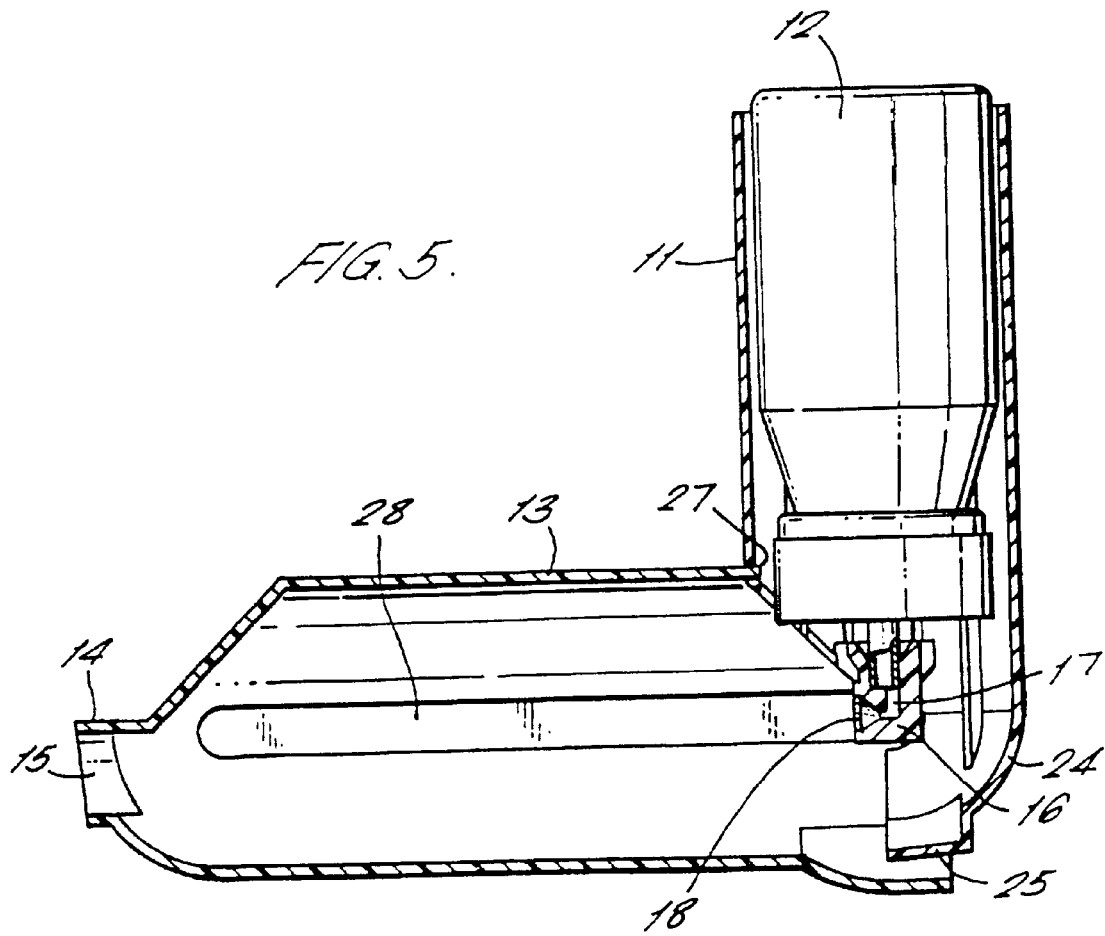

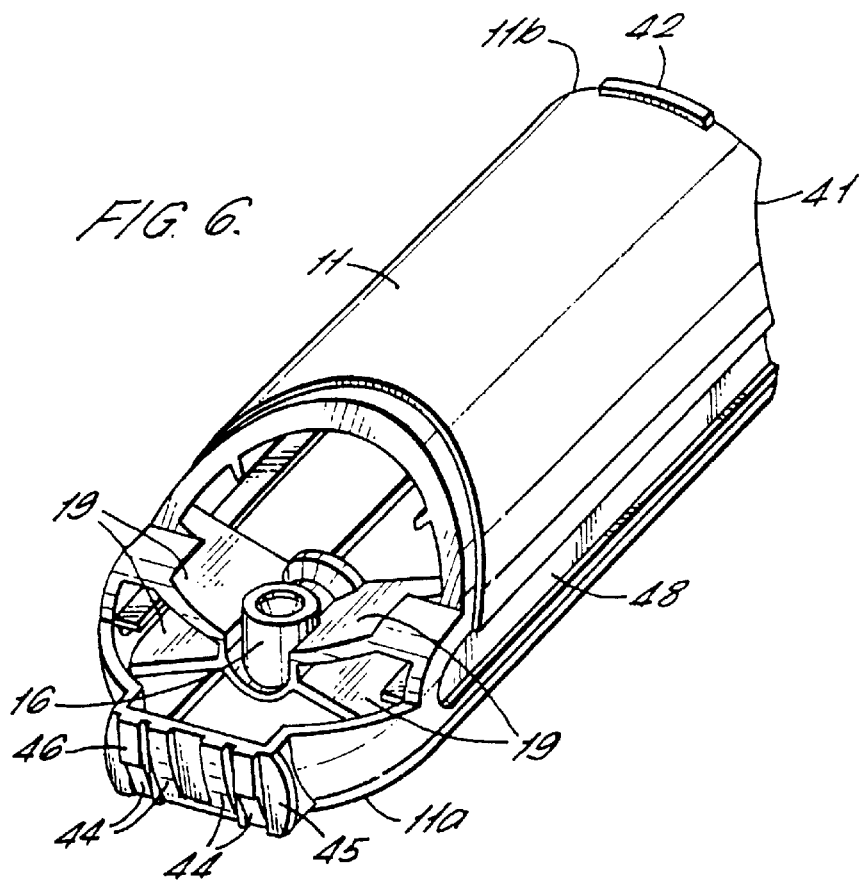
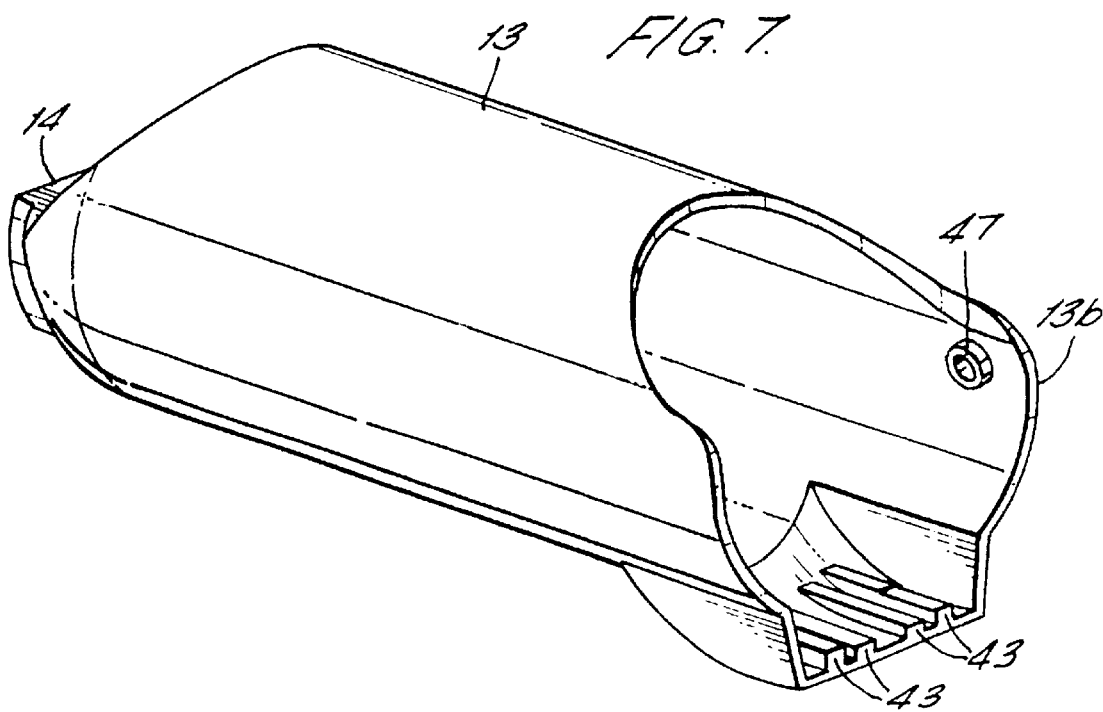

INHALATION DEVICE

This invention relates to an inhalation device for use in enabling material in aerosol form to be dispensed from a container and inhaled by a user.

Inhalers are well-known in medicine for the treatment or alleviation of the symptoms of respiratory complaints such as asthma. One type of conventional inhaler comprises a housing which receives a container of medicament and a spacer member into which the medicament is dispensed and from which it is inhaled by the user through a mouthpiece opening. The medicament enters the spacer member via a nozzle so that it is dispersed into a fine spray before being inhaled. Such a device has an inoperative condition in which the housing enclosing the container is received within the spacer member and an operative condition in which the housing is withdrawn from the spacer member and is pivoted so as to be positioned at an angle to it, typically in the region of 90°. Examples of such devices are described in WO92/20391-A1, EP 0 009 667 and U.S. Pat. No. 3,994, 421.

Existing spacer inhalers of this type are relatively complex constructions. For example, in order to achieve the range of movement between the operative and inoperative positions, conventional inhalers comprise an extra part known as the saddle which is slidably received within the spacer member and to which the housing is pivotally attached.

The present invention aims to provide a simplified design which is easier and cheaper to produce whilst providing improved operation.

In one aspect of the present invention there is provided an inhalation device for use with an aerosol container, the device comprising a housing for receiving an aerosol container and a spacer member defining an outlet through which a user can inhale, the housing and the spacer member being attached together so as to be movable with respect to each other between an inoperative position in which the housing is received within the spacer member and an operative position in which the housing is withdrawn from the spacer member and oriented at a substantial angle thereto, the device further comprising a dispensing member for receiving material to be dispensed from said aerosol container and delivering said material into the spacer member, wherein the dispensing member is located in said housing and is supported spaced from the walls thereof by a plurality of spaced ribs.

This configuration provides improved support for the dispensing member whilst allowing air flow through the housing and into the spacer member, which improves operation as the user inhales. Manufacture of the Preferably, the ribs which support the dispensing member are not equally spaced.

In a preferred embodiment, four ribs are present which may be arranged symmetrically in two pairs.

In a second aspect of the present invention there is provided an inhalation device for use with an aerosol container, the device comprising a housing for receiving an aerosol container and a spacer member defining an outlet through which a user can inhale, the housing and spacer member being attached together so as to be movable with respect to each other between an inoperative position which the housing is received within the spacer member and an operative position in which the housing is withdrawn from the spacer member and oriented at a substantial angle thereto, the device further comprising a dispensing member for receiving material to be dispensed from said aerosol container and delivering it into said spacer member, wherein said spacer member further comprises a forwardly extending mouth piece member defining the outlet and the housing further comprises a forwardly extending projection, shaped so as to be received by said mouthpiece member in the inoperative position in order to close the outlet.

In this way, a separate cap member as used in conventional spacer inhalers to close the outlet in the inoperative position is not required.

Conveniently, the forwardly extending projection and the spacer member are adapted to co-operate with one another in the operative condition in order to retain the housing at a predetermined angle relative to the spacer member.

Preferably, this is achieved by providing the projection and the spacer member with co-operating surfaces which are brought into frictional engagement as the device is moved from the inoperative to the operative condition.

The invention will now be described in detail, by way of example only, with reference to the accompanying drawings in which:

FIG. 1 is a perspective exploded view of a first embodiment of an inhalation device in accordance with the present invention;

FIG. 2 is a perspective view of the inhalation device of FIG. 1 in the inoperative position;

FIG. 3 is an enlarged view of the proximal end of the body portion of the device of FIG. 1;

FIG. 4 is a sectional view of the inhalation device of FIG. 1 in the inoperative position;

FIG. 5 is a sectional view of the inhalation device in the operative position;

FIG. 6 is a perspective view of the housing of an inhalation device in accordance with a second embodiment of the present invention;

FIG. 7 is a perspective view of a spacer member of an inhalation device in accordance with the second embodiment of the invention; and FIG. 8 is a sectional view of the housing and spacer member of FIGS. 6 and 7 connected together in the operative position.

An inhalation device 10 in accordance with a first embodiment of the present invention is illustrated in FIGS. 1 to 5. It comprises a substantially tubular housing 11 which is elliptical in cross-section and which is open at its distal end 11*b* for receiving a conventional container 12 of medicament.

The housing 11 is pivotally connected at its proximal end 11*a* to a substantially tubular spacer member 13 which also has an elliptical cross-section which is larger than that of the housing 11. At its proximal end 13*a*, the spacer member 13 is formed with a mouthpiece member 14 which defines an outlet 15 through which a user may inhale medicament dispensed from the container 12.

The housing 11 and spacer member 13 are preferably made from moulded plastics material.

The inhalation device 10 can be moved between an inoperative position illustrated in FIGS. 2 and 4 and an operative position illustrated in FIG. 5. In the inoperative position, the housing 11 is received within the spacer member 13. In the operative position, the housing 11 is withdrawn from the spacer member 13, pivoted through a substantial angle, e.g in the range of 90° to 105°, and locked in that position.

In order to lock the housing 11 and spacer member 13 in the operative position, the housing is provided with a slot or recess 26 adjacent its proximal edge which is engaged by a locking tab 27 projecting distally from the adjacent edge of the spacer member 13.

The aerosol container 12 received in the housing 11 is provided with a conventional dispensing head 12a which is received by a dispensing member located in the proximal end of the housing 11. The dispensing member comprises a nozzle block 16 which defines a passage 17 which receives medicament dispensed from the container 12. The passage 17 communicates with a nozzle 18 also defined by the nozzle block 16 but which has its axis at a substantial angle, for example in the range of 90° to 105°, to that of the passage 17.

In the operative position of the device 10 as shown in FIG. 5 the nozzle 18 is axially aligned with the spacer member 13. When the end of the container 12 is depressed by a user through the open distal end 11b of the housing 11, medicament is dispensed into the passage 17 and transmitted via the nozzle 18 as a fine spray into the spacer member 13 from which it is inhaled by the user through the outlet 15.

In conventional inhalers, the nozzle block is suspended from the wall of the housing by means of a single stem portion. Alternatively, it may be formed with a solid annular web which completely surrounds it and extends to the walls of the housing. In the present invention, the nozzle block 16 is supported on a plurality, and preferably four, spaced ribs 19 as seen in FIG. 3. The four ribs 19 provide more stable support for the nozzle block 16 than a single support stem and the gaps between the ribs 19 allow for air flow through the body portion and into the spacer member which leads to improved operation of the device 10. Furthermore, the four rib configuration eliminates sink marks and voids which tend to be stem to support the nozzle block. These faults can distort the nozzle block and the nozzle aim. During production, the four rib configuration also makes for a simpler and more efficient mould cavity.

As shown, the four ribs 19 are preferably not equally spaced but are positioned symmetrically in two opposed pairs such that each rib joins the housing wall adjacent one of the cantilever arms 20 which are described further below.

At its proximal end 11a, the housing 11 is formed integrally with two cantilever arms 20 which are diametrically opposed to one another. Each arm 20 has an outwardly projecting trunnion 21 formed at its free end.

At the distal end of the spacer member 13, there are formed a pair of diametrically opposed ears 22 which extend rearwardly, each having a keyhole aperture 23 therethrough.

In the inoperative position of the device 10, when the housing 11 is received within the spacer member 13, the cantilever arms 20 are forced to flex slightly inwardly and the trunnions 21 are slidable against opposite sides of the elliptical interior surface of the spacer member 13. As the housing 11 is withdrawn from this spacer member 13 the trunnions 21 slide along the walls until the cantilever arms 20 are able to relax outwardly so that the trunnions 21 engage in the keyhole apertures 23. The housing 11 may now be pivoted relative to the spacer member about an axis defined by the trunnions 21 and perpendicular to the longitudinal axis of the housing 11 and the spacer member 13.

In order to return the device to the inoperative condition the cantilever arms 20 are flexed inwardly sufficiently to disengage the trunnions 21 from the apertures 23. The housing 11 can now be slid once more into the spacer member 13 with the trunnions 21 sliding along the side walls.

Thus, all the components of the pivot arrangement are formed integrally with either the housing or the spacer member, reducing the complexity and hence the cost of the inhaler. Actuation of the device to move between the operative and inoperative positions is also simplified.

As mentioned above, the spacer member 13 is provided with an outlet 15 through which a user inhales the medicament.

As best seen in FIG. 3, the proximal end 11a of the housing 11 is formed with an extension piece 24 which extends through less than half of the circumference of the housing 11 and which projects proximally of the cantilever arms 20. The extension piece 24 is shaped so as to fit snugly into the outlet 15 defined by the mouthpiece member 14 so that in the inoperative condition, the extension piece 24 acts as a closure member for the outlet 15 to prevent the ingress of dirt or other contaminants.

Thus, the device is integrally formed with a closure member and there is no need for a separate cap or cover as in the prior art which could be lost or even inhaled by a user who had inadvertently left the cap on the inhaler. The number of parts to be produced is also reduced, lowering cost and simplifying manufacture of the device.

A second embodiment of inhalation device in accordance with the present invention will now be described with reference to FIGS. 6 to 8. Many aspects of the second embodiment are the same as those in the first embodiment and thus like reference numerals have been used in the drawings to indicate like parts.

The inhalation device 40 in accordance with the second embodiment once again comprises a tubular housing 11 of elliptical cross-section for receiving a container of medicament and being pivotally connected to a spacer member 13 of larger elliptical cross-section.

An approximately semi-circular cut-out 41 is provided on each side of the distal end 11b of the housing 11 to enable a user to depress the container of medicament 12 which is within the housing in order to dispense the medicament or to enable the user to grasp the container to withdraw it from the housing 11 when it needs to be replaced.

In addition, at the distal end of the housing 11 there is a small thumb tab 42 which is provided to help the user to withdraw the housing 11 from the spacer member 13.

In the second embodiment, the retaining mechanism which holds the housing 11 and spacer member 13 in the operative position comprises a plurality of inwardly extending feet 43 formed at the distal end 13b of the spacer 13 as shown in FIG. 7. A plurality of corresponding outwardly extending feet 44 are formed on the end face 45 of the extension piece 24 provided at the proximal end of the housing 11. When the housing 11 is rotated relative to the spacer member 13, the projecting feet 43 and 44 are brought into frictional engagement with each other so as to retain the housing and the spacer member in the operative position by interference with one another. Preferably, the projecting feet 44 formed on the housing 11 have a curved profile and two or more may be provided with a stepped portion 46. As the housing 11 is rotated towards the operative position, the projecting feet 43 and 44 are gradually brought into closer frictional engagement and eventually snap over the stepped portion 46 into the final operative position.

In the second embodiment, in order to provide pivotal engagement between the housing 11 and the spacer member 13, the spacer member 13 is provided with a pair of opposed inwardly projecting trunnions 47 at its distal end 13b (only one of which is visible in FIG. 7). A pair of opposed axially extending slots 48 are formed in the outer surface of the housing 11 to receive the trunnions 47. Thus, in the inoperative position, the housing 11 is located within the spacer member 13 in the same manner as in the first embodiment.

To reach the operative position, the housing 11 is withdrawn from the spacer member 13 with each trunnion 47 running in a respective slot 48. In the fully retracted position, the trunnions 47 are located at the blind end of each slot 48 at the proximal end 11a of the housing 11 and the housing 11 may then be pivoted with respect to the spacer member 13 about an axis defined by the trunnions 47.

Finally, in FIG. 8 it can be seen that the inner surface of the housing 11 is provided with a number of inwardly projecting ribs 49 which serve to locate the medicament container 12 centrally within the housing 11 so that the dispensing member 12a will easily locate into the nozzle block 16. It will be apparent that such ribs together with other features such as the cutouts 41, thumb tab 42 and inter-engaging feet 43 and 44 although described with reference to the second embodiment are equally applicable to the first embodiment in addition to or instead of the corresponding features of the first embodiment.

From the foregoing it will be apparent that the present invention provides an improved inhalation device with fewer parts which is easier to make and assemble and which provides improved operation in use.

What is claimed is:

1. An inhalation device for use with an aerosol container, the device comprising a housing for receiving an aerosol container and a spacer member defining an outlet through which a user can inhale, the housing and the spacer member being attached together so as to be movable with respect to each other between an inoperative position in which the housing is received within the spacer member and an operative position in which the hosing is withdrawn from the spacer member and oriented at a substantial angle thereto, the device further comprising a dispensing member for receiving material to be dispensed from said container and delivering it into said spacer member, wherein the spacer member further comprises a forwardly extending mouthpiece member defining the outlet and characterized in that a proximal end of the housing further comprises a projection shaped so as to be received by said mouthpiece member in the inoperative condition whereby the projection acts as a closure member to close the outlet.

2. An inhalation device as claimed in claim 1, wherein the projection and spacer member are adapted to co-operate with one another in the operative condition in order to retain the housing at a predetermined angle relative to the spacer member.

3. An inhalation device as claimed in claim 2, wherein the projection and spacer member are provided with co-operating surfaces which are brought into frictional engagement as the device is moved from the inoperative to the operative position.

4. An inhalation device as claimed in claim 1, wherein the dispensing member is located in said housing and supported spaced from the walls thereof by a plurality of spaced ribs.

5. An inhalation device as claimed in claim 4, wherein the plurality of ribs are not equally spaced.

6. An inhalation device as claimed in claim 4, wherein there are four ribs.

7. An inhalation device as claimed in claim 6, wherein the four ribs are arranged symmetrically in two pairs.

* * * * *